(12) United States Patent
Kahlert et al.

(10) Patent No.: US 11,769,579 B2
(45) Date of Patent: Sep. 26, 2023

(54) FACILITATING PULMONARY AND SYSTEMIC HEMODYNAMICS

(71) Applicant: KONINKLIJKE PHILIPS N.V., Eindhoven (NL)

(72) Inventors: Joachim Kahlert, Aachen (DE); Calina Ciuhu, Eindhoven (NL); Maarten Petrus Joseph Kuenen, Veldhoven (NL); Rick Bezemer, Amsterdam (NL); Laurentia Johanna Huijbregts, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 1053 days.

(21) Appl. No.: 16/471,150

(22) PCT Filed: Dec. 20, 2017

(86) PCT No.: PCT/EP2017/083691
§ 371 (c)(1),
(2) Date: Jun. 19, 2019

(87) PCT Pub. No.: WO2018/115047
PCT Pub. Date: Jun. 28, 2018

(65) Prior Publication Data
US 2020/0043591 A1 Feb. 6, 2020

Related U.S. Application Data

(60) Provisional application No. 62/436,465, filed on Dec. 20, 2016.

(51) Int. Cl.
*G16H 20/30* (2018.01)
*A61M 16/00* (2006.01)
(Continued)

(52) U.S. Cl.
CPC .......... *G16H 20/30* (2018.01); *A61B 5/0082* (2013.01); *A61B 5/0295* (2013.01); *A61M 16/024* (2017.08); *A61M 16/0003* (2014.02)

(58) Field of Classification Search
CPC ............ A61M 16/0003; A61M 16/024; A61B 5/0082; A61B 5/0295; G16H 20/30
See application file for complete search history.

(56) References Cited

U.S. PATENT DOCUMENTS

| 4,676,232 A | 6/1987 | Olsson |
| 5,377,671 A | 1/1995 | Biondi |

(Continued)

FOREIGN PATENT DOCUMENTS

| EP | 1264615 | 12/2002 |
| WO | 2013/179181 | 12/2013 |
| WO | 2018115082 | 6/2018 |

OTHER PUBLICATIONS

International Search Report and Written Opinion dated Mar. 23, 2018 for International Application No. PCT/EP2017/083691 filed Dec. 20, 2017.

*Primary Examiner* — Lynsey C Eiseman
*Assistant Examiner* — Amanda L. Steinberg
(74) *Attorney, Agent, or Firm* — Daniel H. Brean; Andrew M. Gabriel

(57) ABSTRACT

The present disclosure pertains to a system and method for monitoring and for facilitating pulmonary and systemic hemodynamics in the treatment and/or prevention of cardiac arrhythmias or structural cardiac changes, caused by altered preload. The system comprises: a pressure generator; a first sensor configured to generate output signals conveying information related to venous blood accumulation during cardiac preload in the subject; a second sensor configured to generate output signals conveying information related to systemic arterial circulation in the subject; and one or more hardware processors configured by machine-readable instructions to control the pressure generator to adjust the pressure levels of the flow of breathable gas during one or (Continued)

both of inhalation and exhalation to facilitate the pulmonary and systemic circulation based on the output signals from the first sensor and the second sensor.

20 Claims, 11 Drawing Sheets

(51) Int. Cl.
*A61B 5/00* (2006.01)
*A61B 5/0295* (2006.01)

(56) References Cited

U.S. PATENT DOCUMENTS

| | | | |
|---|---|---|---|
| 7,314,449 B2 | 1/2008 | Pfeiffer | |
| 9,504,400 B2 | 11/2016 | Watanabe | |
| 2004/0230108 A1* | 11/2004 | Melker | A61B 5/6829 |
| | | | 128/204.23 |
| 2005/0109339 A1 | 5/2005 | Stehmann | |
| 2008/0066753 A1* | 3/2008 | Martin | A61M 16/0057 |
| | | | 128/204.23 |
| 2009/0281399 A1* | 11/2009 | Keel | A61B 5/02158 |
| | | | 600/513 |
| 2012/0209345 A1* | 8/2012 | Shkurovich | G16H 20/30 |
| | | | 607/23 |
| 2012/0296216 A1* | 11/2012 | Sharf | A61B 8/4209 |
| | | | 600/459 |
| 2014/0058273 A1* | 2/2014 | Theran | A61B 5/0295 |
| | | | 600/480 |

* cited by examiner

FACILITATING PULMONARY AND SYSTEMIC HEMODYNAMICS

CROSS-REFERENCE TO RELATED APPLICATIONS

This patent application claims the priority benefit under 35 U.S.C. § 371 of international patent application no. PCT/EP2017/083691, filed Dec. 20, 2017, which claims the priority benefit under 35 U.S.C. § 119(e) of U.S. Provisional Application No. 62/436,465 filed on Dec. 20, 2016, the contents of which are herein incorporated by reference.

BACKGROUND OF THE INVENTION

1. Field of the Invention

The present disclosure pertains to a system and method for monitoring and for facilitating pulmonary and systemic hemodynamics in the treatment and/or prevention of cardiac arrhythmias or structural cardiac changes, caused by altered preload.

2. Description of the Related Art

Pressure support respiratory therapy systems are known. Typically, pressure support therapy system parameters (e.g., pressure levels, volumes, rates, etc.) are configured to ensure a subject receives adequate airflow. Pressure support therapy systems are not typically configured to monitor and/or influence hemodynamics in the subject.

SUMMARY OF THE INVENTION

Accordingly, one or more aspects of the present disclosure relate to a sensing system to monitor changes in the atrial preload and a ventilation support system configured to facilitate pulmonary and systemic circulation in a subject. The system comprises a pressure generator, first and second sensors, one or more hardware processors, and/or other components. The pressure generator is configured to generate a pressurized flow of breathable gas for delivery to an airway of the subject according to a pressure support therapy regime. The pressure support therapy regime indicates pressure levels of the pressurized flow of breathable gas provided by the pressure generator during inhalation and exhalation by the subject. The first sensor is configured to generate output signals conveying information related to venous blood accumulation during cardiac and respiratory cycles in the subject. The second sensor is configured to generate output signals conveying information related to atrial blood volume overloading and alterations in cardiac preload and afterload in the subject. Preload is the end-diastolic pressure in the atrium. By the given compliance it can also be the end-diastolic blood volume in the atrium. So, a change of the preload is both a change of the pressure and the blood volume. As described herein, the present system measures the change in the volume, so it is a volume centric view on preload and preload alterations. The same holds for the afterload. It is both the end systolic pressure and/or blood volume. In the present volumetric view an afterload change is the change of the outflowing blood volume which corresponds to a change in the stroke volume. The one or more hardware processors are configured by machine-readable instructions to control the pressure generator to adjust the pressure levels of the pressurized flow of breathable gas during one or both of inhalation and exhalation to facilitate the pulmonary and systemic circulation based on the output signals from the first sensor and the second sensor.

Another aspect of the present disclosure relates to a ventilation support method for facilitating pulmonary and systemic circulation in a subject with a ventilation support system. The system comprises a pressure generator, a first sensor, a second sensor, one or more hardware processors, and/or other components. The method comprises generating, with the pressure generator, a pressurized flow of breathable gas for delivery to an airway of the subject according to a pressure support therapy regime. The pressure support therapy regime indicates pressure levels of the pressurized flow of breathable gas provided by the pressure generator during inhalation and exhalation by the subject. The method further comprises: generating, with the first sensor, output signals conveying information related to venous blood accumulation during cardiac and respiratory cycles in the subject; generating, with the second sensor, output signals conveying information related to atrial blood volume and cardiac preload/afterload in the subject; and controlling, with the one or more hardware processors, the pressure generator to adjust the pressure levels of the pressurized flow of breathable gas during one or both of inhalation and exhalation to facilitate the pulmonary and systemic circulation based on the output signals from the first sensor and the second sensor.

Still another aspect of the present disclosure relates to system configured to facilitate pulmonary and systemic circulation in a subject. The system comprises: means for generating a pressurized flow of breathable gas for delivery to an airway of the subject according to a pressure support therapy regime, the pressure support therapy regime indicating pressure levels of the pressurized flow of breathable gas provided by the pressure generator during inhalation and exhalation by the subject; means for generating output signals conveying information related to venous blood accumulation during cardiac cycle in the subject; means for generating output signals conveying information related to blood volume, cardiac preload and blood volume and preload changes in the subject; and means for controlling the means for generating the pressurized flow of breathable gas to adjust the pressure levels of the pressurized flow of breathable gas during one or both of inhalation and exhalation to facilitate the pulmonary and systemic circulation based on the output signals from the means for generating output signals conveying information related to the venous blood accumulation and the means for generating output signals conveying information related to blood volume and cardiac preload and blood volume and preload changes.

These and other features and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
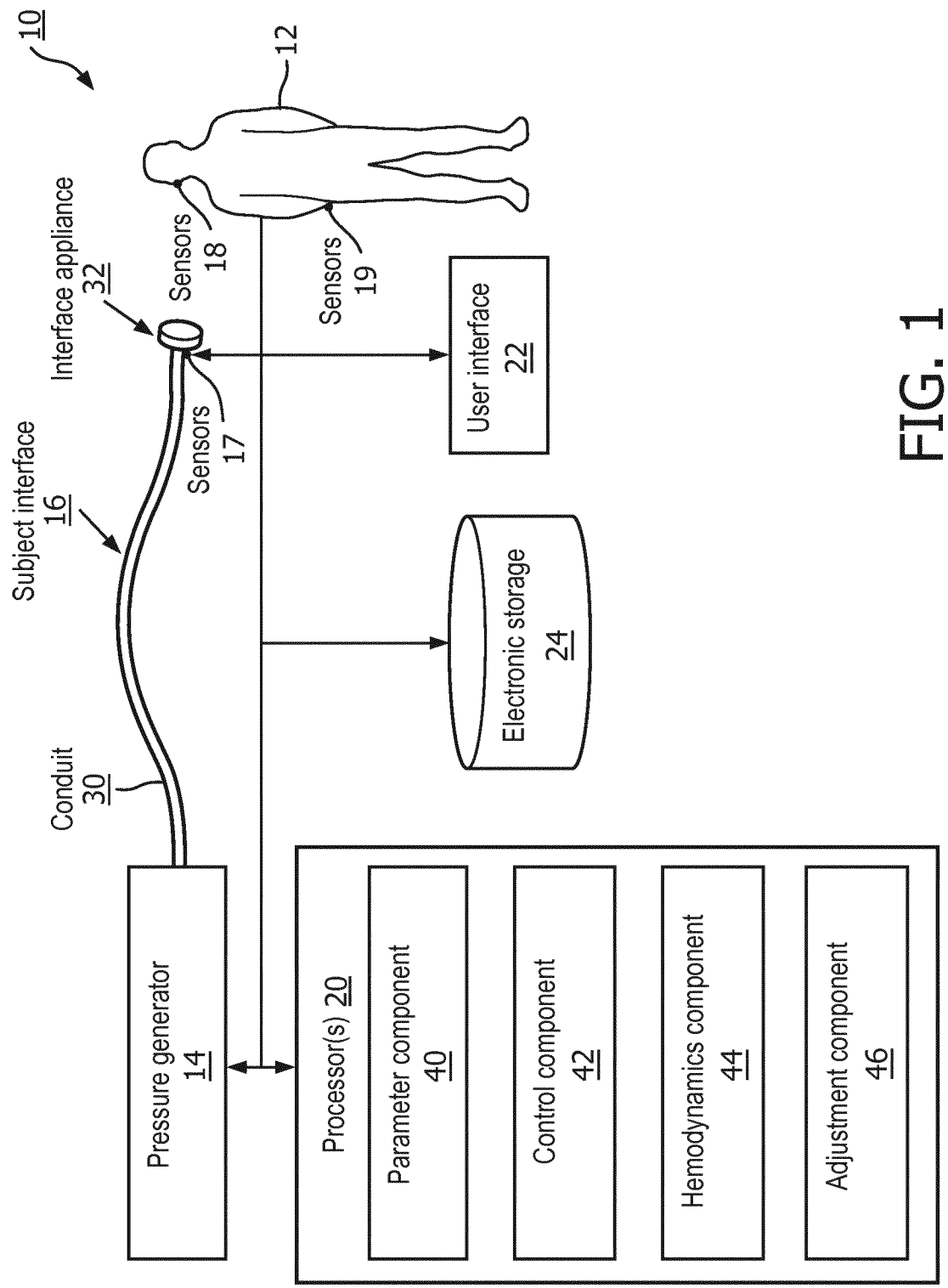
FIG. 1 is a schematic illustration of a ventilation support system configured to facilitate pulmonary and systemic circulation in a subject.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other. As used herein, "removably coupled" means that two elements are able to be separated and/or rejoined with each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 is a schematic illustration of a ventilation support system 10 configured to facilitate pulmonary and systemic circulation in a subject 12. System 10 is configured to assist the heart to balance pulmonary hemodynamics, to discourage and/or reverse cardiac overloading (including overstretching and/or dilatation of atria), to discourage and/or prevent the development of structural cardiac changes, atrial fibrillation, and/or perform other operations. Paroxysmal atrial fibrillation (Afib) is higher in subjects suffering from sleep apnea. These subjects often experience episodes of paroxysmal Afib during sleep. Many subjects who develop obstructive sleep apnea (OSA) also develop chronic persistent Afib. During an OSA event the intrathoracic pressure in subject 12 builds (e.g., as a negative pressure), which increases the venous return flow to the heart. This results in an increased preload of the right atrium, which causes a volume overloading of the right atrium and an activation of mechanical stretch receptors, the Bainbridge receptors, located both in the right atrium and the left atrium. The volume overloading causes stretching and dilatation of the atria and can, over the long term, cause a structural change of the atria. The structural change of the atria and the activation of the Bainbridge receptors contribute to the development of cardiac arrhythmias and consequent development of persistent Afib.

Similarly, subjects with enlarged hearts and low resting heart rates (e.g., endurance athletes and/or other subjects), who require large stroke volumes, are also prone to Afib episodes. For example, during sleep, the heart rate of such subjects may become very low, leading to long cardiac filling times, and higher stroke volumes. This induces higher stress (atrial stretching) on the heart, which can lead to Afib. The likelihood of Afib in such subjects is also increased by high intrathoracic pressure changes that arise because of the very slow breathing rate in such subjects during sleep.

Figure 2:
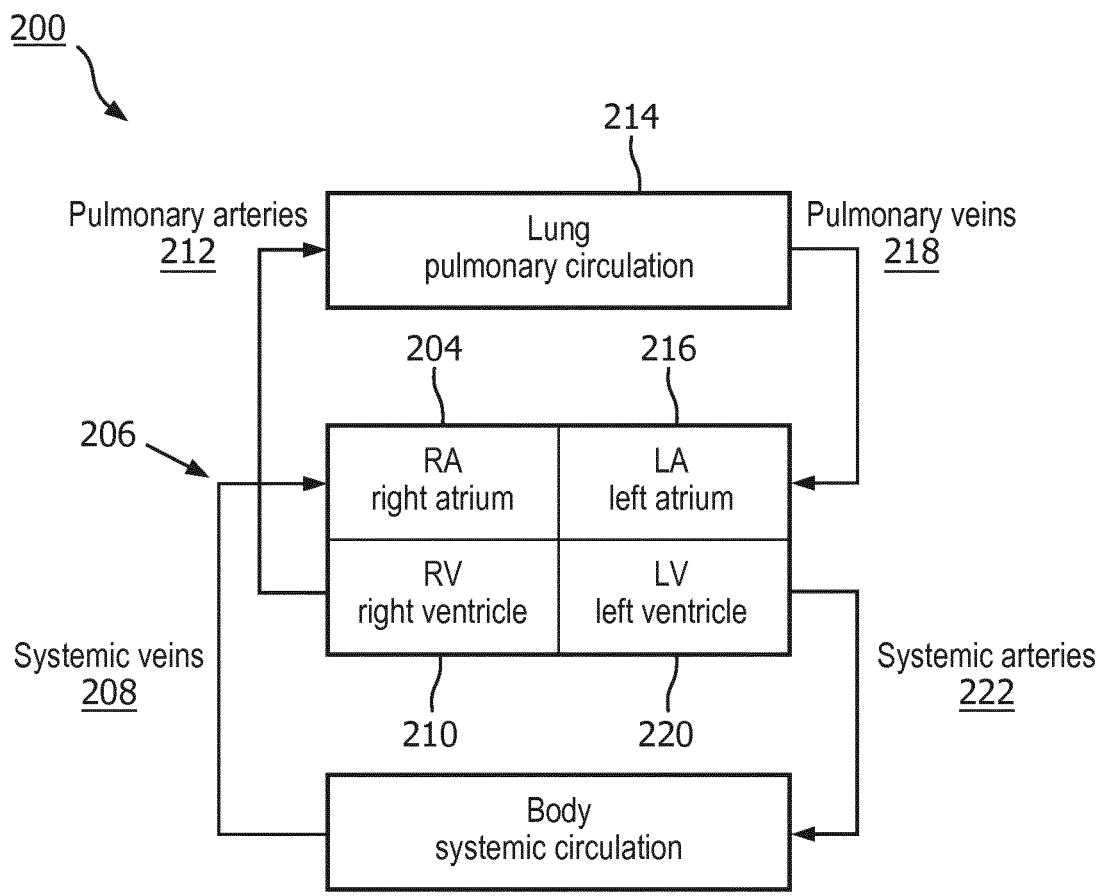
FIG. 2 is a schematic illustration of a circulatory system.

FIG. 2 is a schematic illustration of a circulatory system 200. As shown in FIG. 2, blood from the systemic circulation system 202 of the body is received by the right atrium 204 of the heart 206 via systemic veins 208. Blood from the right ventricle 210 passes through the pulmonary arteries 212 into the pulmonary circulation system 214 of the lungs, then back to the left atrium 216 of heart 206 via pulmonary veins 218. Blood from the left ventricle 220 of heart 206 is pumped via systemic arteries 222 through systemic circulation system 202.

Returning to FIG. 1, in a given subject 12, the respiration muscles (e.g., the ribcage muscles and the diaphragm) act as a pulmonary muscle pump. During inhalation the thorax widens and the intrathoracic pressure (e.g., the intra pleural pressure) builds (e.g., as a negative pressure). This intrathoracic pressure has several hemodynamic effects. For example, the pressure increases the venous return flow from the extra-thoracic systemic veins into the vena cava. This increased venous return increases the preload of the right atrium and the loading of the right ventricle. Over an extended period of time, the increased preload repeatedly dilates the right atrium, and may cause permanent structural changes, and changes of the electrophysiological pathways in the atria, which can cause arrhythmias, and consequent development of Afib (e.g., as described above). In addition, the pressure impacts the pulmonary blood vessels (e.g., the extra-alveolar vessels). The intra pleural pressure changes the transmural pressure on the pulmonary vessels. The high compliance of the pulmonary vessels causes the pulmonary vessels to widen or constrict when the pressure of the blood in the vessels changes. The increased intrathoracic pressure causes an increased accumulation of blood in the pulmonary vessels. This correlates with a decrease of the vascular resistance of the extra-alveolar vessels, which has hemodynamic consequences on the flow velocity and the blood pressure, for example.

Figure 3:
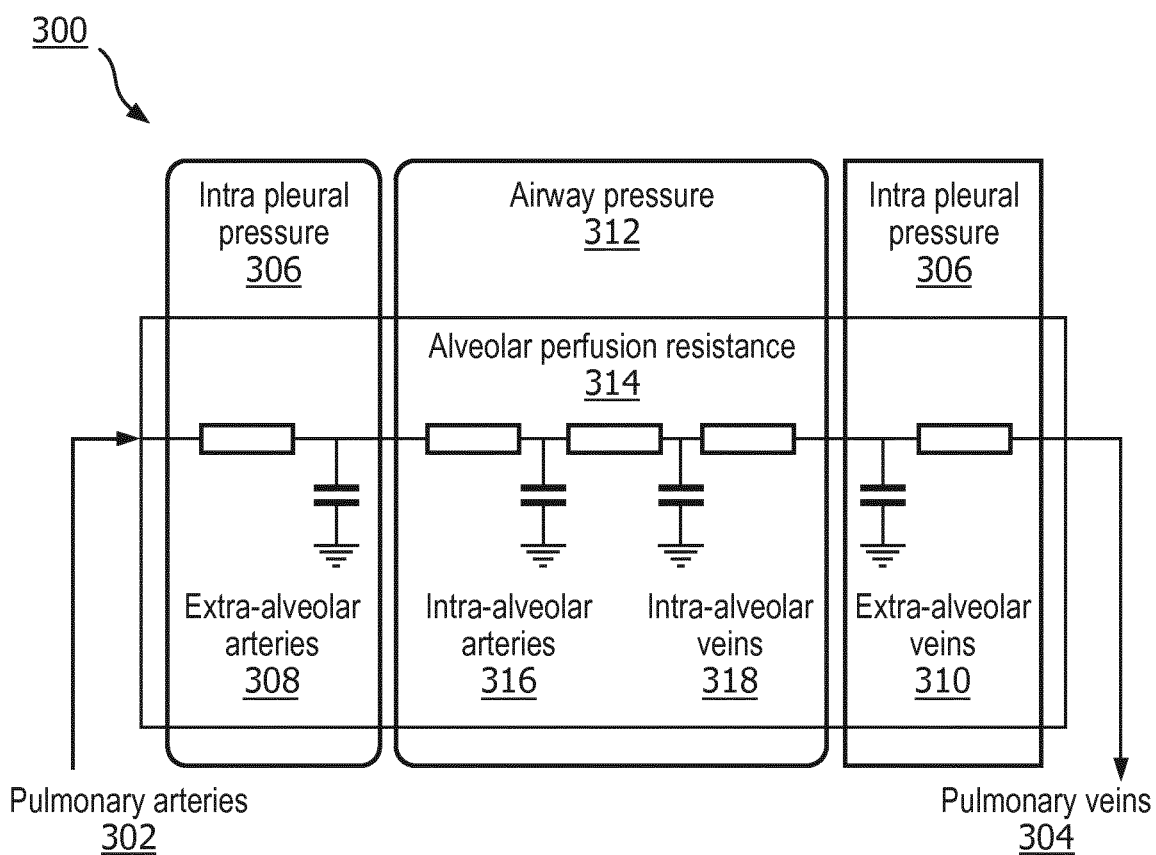
FIG. 3 is a schematic illustration of a pulmonary circulation system.

FIG. 3 illustrates a pulmonary circulation system 300. As shown in FIG. 3, blood enters pulmonary circulation system 300 via pulmonary arteries 302 and leaves pulmonary circulation system 300 via pulmonary veins 304. Intra pleural pressure 306 (described above) influences extra-alveolar arteries 308 and extra-alveolar veins 310, while airway pressure 312 influences alveolar perfusion resistance 314, intra-alveolar arteries 316, and intra-alveolar veins 318. The pulmonary circulation depends on the respiration cycle, respiration depth and the airway pressure. A device-assisted control of respiration and airway pressure offers therapeutic options in the control of the pulmonary blood flow, the pressure in the pulmonary veins and the blood accumulation. It should be noted, however, that this invention may be applied to both spontaneously breathing patients and mechanically assisted patients. The pressure-control may different in each situation but the principles described herein apply to both situations.

Muscular effort during exhalation turns the thoracic pressure from a "negative" pressure into a "positive" pressure, but nonetheless pressurizes the venous system. The pressure caused by the muscular effort acts as a transmural force on the extra-alveolar vessels. This force compresses the extra-alveolar vessels and creates a blood flow out of the vessels. The pressure swing between inhalation and exhalation acts physiologically as a pulmonary muscle pump such that blood is pumped from the extra-alveolar vessels into the intra-alveolar arterioles and/or capillaries. However, a backpressure wave may also occur, which forces blood to flow back into the right ventricle (FIG. 2). For example, if the heart is in the systolic phase of the cardiac cycle, the pulmonary valve is open and the backpressure wave causes a backflow into the right ventricle. If the heart is in the diastolic phase the pulmonary valve is closed and no back flow occurs into the right ventricle. However, during exhalation, when the heart is in the diastolic phase, blood flows into the intra-alveolar arteries and capillaries. This respiration related additional transmural pressure leads to an increase of the pulmonary arterial blood pressure. As such, an increased transmural pressure results in an increased pulmonary arterial pressure. Scenarios like these may occur, for example, during physical exercise, during a stay in higher altitudes, etc., when the respiration drive is increased. Scenarios like these may also occur in subjects suffering from an obstructed upper airway and/or suffering from a restricted pulmonary airflow (e.g., asthma, congested bronchiole, etc.).

Returning to FIG. 1, as described above, intrathoracic pressure (e.g., "positive" or "negative") causes changes in the thoracic hemodynamics and blood volume overloading. System 10 is configured to lower the required muscular effort for breathing, and lower (e.g., increase a "negative" pressure and/or decrease a "positive" pressure) the intrathoracic pressure, which consequently lowers the transmural force on the pulmonary vessels. Typical positive pressure support therapy devices (e.g., CPAP devices) do not monitor the hemodynamics described above. Parameter set points in such devices are not set to levels which treat the hemodynamic conditions caused by an obstructive respiration disorder, for example. Traditionally, ventilation support (e.g. CPAP, etc.) devices have been developed to control parameters such as the tidal volume, the minute volume, etc., during breathing. In contrast, system 10 is configured to lower the work of breathing.

Pressure support therapy may be used by system 10 to lower the muscular effort required for breathing (e.g., the respiration drive) and reduce preload related cardiac stress, rather than merely using pressure support therapy to ensure subject 12 receives adequate airflow. System 10 is configured to monitor and control volume overloading in pulmonary circulation. System 10 is configured to monitor the trans-pulmonary delay/transfer/transit time and use pressure support therapy to control the venous return blood flow to the right and left atriums. In this context delay/transfer/transit time is the time a volumetric change in the right atrial preload takes before a volumetric change in the afterload of the left ventricle (change in LV stroke volume) can be measured.

As described herein, system 10 is configured to discourage and/or prevent hemodynamic cardiac stress (atrial stretch by volume overloading) using ventilation support using hemodynamic vital sign information to determine therapy pressures. Advantageously, system 10 reduces and/or prevents volume overloading of the atria and ventricles. System 10 is configured to cause a decrease in the volume of accumulated blood in pulmonary circulation. System 10 is configured to lower the preload to discourage and/or prevent atrial dilatation and/or activation of the stretch receptors (e.g., the Bainbridge receptors) in the atria. System 10 is configured to lower the amount of blood in the venous return and reduce the end-systolic blood accumulation. System 10 is configured to lower the required inspiratory muscular breathing effort. System 10 is configured to reduce the intrathoracic pressure swing (e.g., the difference between the "positive" intrathoracic pressure and the "negative" intrathoracic pressure) during breathing. System 10 is configured to reduce and/or end paroxysmal Afib by discouraging and/or reversing atrial dilatation.

In some embodiments, system 10 comprises one or more of a pressure generator 14, a subject interface 16, one or more sensors 17, 18, 19, one or more processors 20, a user interface 22, electronic storage 24, and/or other components.

Pressure generator 14 is configured to generate a pressurized flow of breathable gas for delivery to the airway of subject 12. Pressure generator 14 is configured to generate the pressurized flow of breathable gas for delivery to the airway of subject 12 according to a pressure support therapy regime. The pressure support therapy regime indicates pressure levels of the pressurized flow of breathable gas provided by pressure generator 14 during inhalation and exhalation by subject 12 and/or other information. Pressure generator 14 may control one or more ventilation parameters of the flow of gas (e.g., rates, pressures, volumes, temperatures, compositions, etc.) for therapeutic purposes, and/or for other purposes. Pressure generator 14 is configured to control one or more ventilation parameters of the pressurized flow of breathable gas according to a prescribed pressure support therapy regime and/or other therapy regimes. By way of a non-limiting example, pressure generator 14 may be configured to control ventilation parameters such as a breath rate, a flow rate, a pressure support positive end expiratory pressure (PEEP), a tidal volume, a minute volume, an inspiratory to expiratory breath phase ratio (e.g., an I:E ratio), inhalation pressure levels, exhalation pressure levels, and/or other ventilation parameters of the flow of gas to provide pressure support.

Pressure generator 14 receives a flow of gas from a gas source, such as the ambient atmosphere, and elevates and/or reduces the pressure of that gas for delivery to the airway of subject 12. Pressure generator 14 is and/or includes any device, such as, for example, a pump, blower, piston, or bellows, that is capable of elevating and/or reducing the pressure of the received gas for delivery to a patient. Pressure generator 14 may comprise servo controlled valves and/or motors, one or more other valves and/or motors for controlling the pressure and/or flow of gas, and/or other components for generating and/or controlling the pressurized flow of breathable gas. The present disclosure also contemplates controlling the operating speed of the blower, either alone or in combination with such valves, to control the pressure and/or flow of gas provided to the patient.

Subject interface 16 is configured to deliver the pressurized flow of breathable gas to the airway of subject 12. As such, subject interface 16 comprises conduit 30, interface appliance 32, and/or other components. Conduit 30 is configured to convey the pressurized flow of gas to interface appliance 32. Conduit 30 may be a flexible length of hose, or other conduit that places interface appliance 32 in fluid communication with pressure generator 14. Interface appliance 32 is configured to deliver the flow of gas to the airway of subject 12. In some embodiments, interface appliance 32 is non-invasive. As such, interface appliance 32 non-invasively engages subject 12. Non-invasive engagement comprises removably engaging an area (or areas) surrounding one or more external orifices of the airway of subject 12 (e.g., nostrils and/or mouth) to communicate gas between the airway of subject 12 and interface appliance 32. Some examples of non-invasive interface appliance 32 may comprise, for example, a nasal cannula, a nasal mask, a nasal/oral mask, a full face mask, a total face mask, or other interface appliances that communicate a flow of gas with an airway of a subject. The present disclosure is not limited to these examples, and contemplates delivery of the flow of gas to the subject using any interface appliance, including an invasive interface appliance such as an endotracheal tube and/or other appliances.

Sensors 17 are configured to generate output signals conveying information related to the ventilation of subject 12 and/or other gas and/or breathing parameters. In some embodiments, the information related to the ventilation of subject 12 includes the flow rate (and/or information related to the flow rate) of the pressurized flow of breathable gas, the $CO_2$ concentration (and/or information related to the $CO_2$ concentration such as the partial pressure of $CO_2$ and/or other information) in the pressurized flow of breathable gas, and/or other information. In some embodiments, the information related to other gas and/or breathing parameters may comprise information related to volumes (e.g., tidal volume, minute volume, etc.), pressures (e.g., inhalation pressure level, exhalation pressure level, etc.), other compositions (e.g., concentration(s)) of one or more constituent gasses, a gas temperature, a gas humidity, acceleration, velocity, acoustics, changes in a parameter indicative of respiratory effort by subject 12, and/or other parameters. Sensors 17 may comprise one or more sensors that measure such parameters directly (e.g., through fluid communication with the flow of gas in subject interface 16). Sensors 17 may comprise one or more sensors that generate output signals related to one or more parameters of the flow of gas indirectly. For example, one or more of sensors 17 may generate an output based on an operating parameter of pressure generator 14 (e.g., a valve driver or motor current, voltage, rotational velocity, and/or other operating parameters). Although sensors 17 are illustrated at a single location within (or in communication with) conduit 30 between interface appliance 32 and pressure generator 14, this is not intended to be limiting. Sensors 17 may include sensors disposed in a plurality of locations, such as for example, within pressure generator 14, within (or in communication with) interface appliance 32, in communication with subject 12, and/or in other locations. For example, sensors 17 may include a flow rate sensor, a capnography sensor (configured to generate output signals conveying information related to a concentration of $CO_2$ in the pressurized flow of breathable gas), a volume sensor, a pressure sensor, a temperature sensor, an acoustic sensor, and/or other sensors located at various locations in system 10.

Sensor 18 is configured to generate output signals conveying information related to venous blood accumulation during cardiac and respiratory cycles in subject 12. In some embodiments, sensor 18 is and/or includes a sublingual photoplethysmography (PPG) sensor configured to generate output signals that convey information related to a blood volume variation at the anatomical area at and around a sublingual vein modulated by a respiration cycle and a beating heart of subject 12. Sensor 18 may monitor blood accumulation by generating output signals conveying information related to dilation of the jugular vein and/or a branch of the jugular vein such as the sublingual vein and/or other veins. In some embodiments, the information in the output signals of sensor 18 may be used to determine the right atrium preload, for example.

In some embodiments, sensor 18 generates output signals conveying information related to accumulated venous blood over time modulated by the respiration cycle and the beating heart in subject 12. In some embodiments, sensor 18 comprises components configured for remote and/or contact monitoring using laser Doppler, laser speckle, ultrasound Doppler and imaging, (electro)magnetic sensing, and/or NIRS.

At onsets of individual respiration cycles (e.g., at the onset of inhalation) the cardiac preload is increased, which leads to an increased filling of the right atrium and an increase right ventricular stroke volume (RV-SV). This increased RV-SV creates a stronger blood flow (wave) through the pulmonary vessels. This increased pulmonary blood flow can be measured as an increased and delayed left ventricular stroke volume. The delay of the increased stroke volume corresponds to the pulmonary transfer time measurable in the systemic arteries (e.g., by sensor 19 described below). As described above, in some embodiments, sensor 18 may be implemented by optical means like Laser Doppler or laserspeckle and/or any other optical means, Ultrasound Doppler, and/or bio-impedance sensing or near infrared spectroscopy (NIRS). The sensors could be either in contact or non-contact mode.

Sensor 19 is configured to generate output signals conveying information related to the heart activity and/or the systemic arterial circulation in subject 12. In some embodiments, sensor 19 includes sensor 18; a systemic PPG sensor configured to removably couple with a forehead, temple, ear, finger, and/or other portion of subject 12; and/or other components. In some embodiments, sensor 19 comprises electrocardiogram (ECG) electrodes, an accelerometer, radio frequency (RF) sensors, radar, a microphone, a camera, and/or other sensors configured to generate output signals conveying information related to a heart rhythm of subject 12. In some embodiments, one or more such sensors (e.g., a microphone, a camera, etc.) may be included in a smartphone and configured to communicate wirelessly with one or more other components of system 10.

In some embodiments, sensor 19 is configured such that generating output signals conveying information related to left ventricular afterload includes generating output signals that convey information related to the increased and delayed blood flow (wave) in the systemic arteries and arterioles (e.g., as described above related to sensor 18). The delay or transfer time (the delayed arrival of the blood flow (wave)) corresponds to the anatomical structures of the blood vessels and cardiac chambers in subject 12. The delay/transfer time is a function of the flow resistance and the capacitive behavior of the pulmonary vessels in subject 12. The volume of accumulated blood in the pulmonary vessels changes with a modulated blood wave. Therefore, the delay/transfer time may be a surrogate representative of the accumulated blood in the right atrium, the pulmonary veins, and the left atrium of subject 12. The delay/transfer time is measured and determined by the time delay of the respiration-induced modulation in the signal of sensor 18 compared with the modulated signal of sensor 19 (see FIG. 5B and its corresponding description below).

Figure 4:
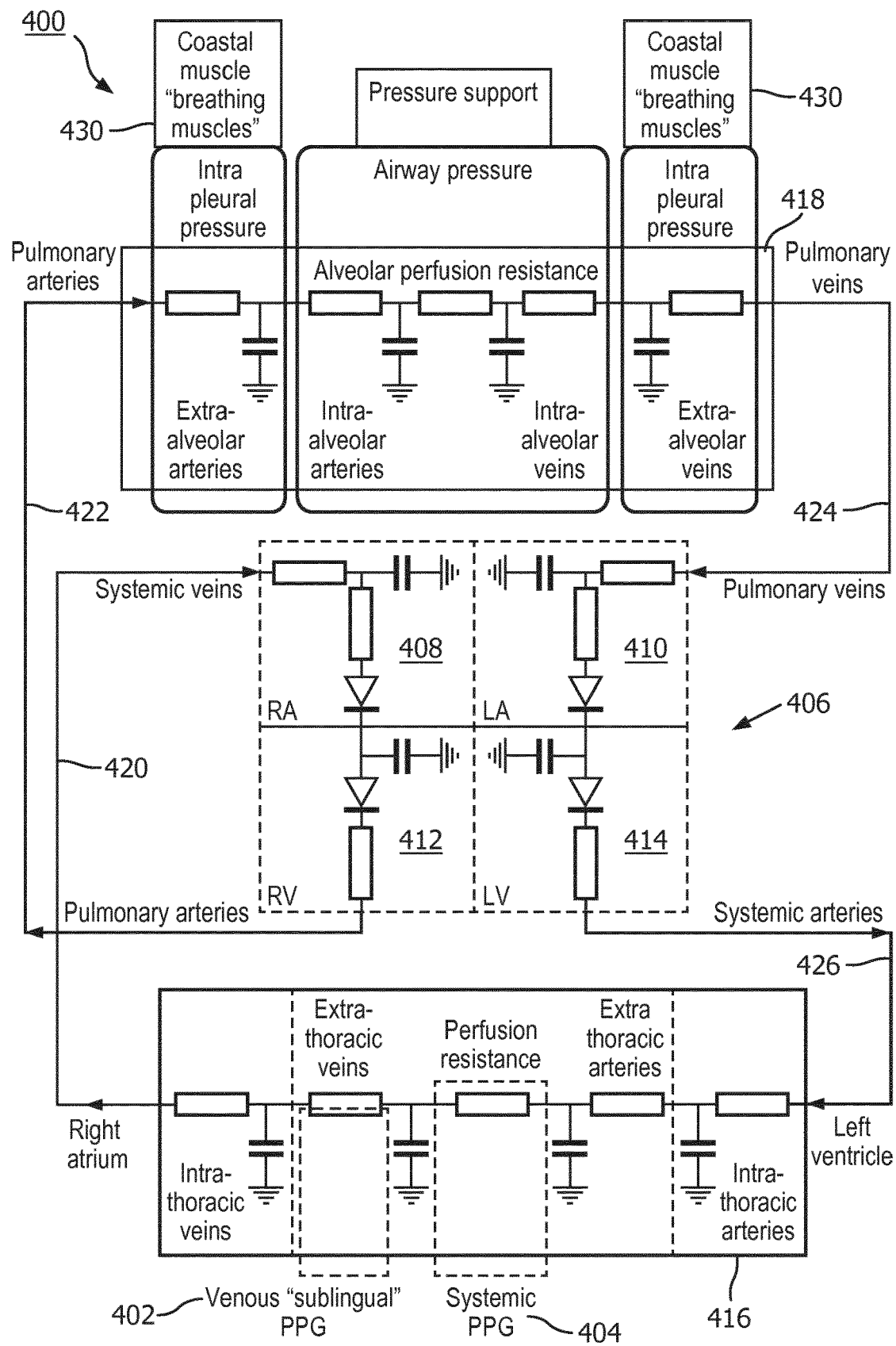
FIG. 4 illustrates a venous sublingual PPG sensor and a systemic PPG sensor in a schematic illustration of a circulatory system.

FIG. 4 illustrates a venous sublingual PPG sensor 402 (e.g., sensor 18 shown in FIG. 1) and a systemic PPG sensor 404 (e.g., sensor 19 shown in FIG. 1) relative to a schematic illustration of a circulatory system 400. Circulatory system 400 includes a heart 406 (comprising right atrium 408, left atrium 410, right ventricle 412, and left ventricle 414), systemic circulation system 416, and pulmonary circulation system 418. Blood from systemic circulation system 416 is received by right atrium 408 of heart 406 via systemic veins 420. Blood from the right ventricle 412 passes through pulmonary arteries 422 into pulmonary circulation system 418, then back to left atrium 410 of heart 406 via pulmonary veins. Blood from left ventricle 414 of heart 406 is pumped through systemic arteries 426 through systemic circulation system 416. As shown in FIG. 4, the coastal "breathing" muscles 430 influence the intra pleural pressure, and in turn the extra-alveolar arteries and veins. Pressure support therapy 432 influences the airway pressure, and in turn alveolar perfusion resistance and the intra-alveolar arteries and veins.

It should be noted that in some embodiments, system 10 (FIG. 1) only need include one of the sensors 17, 18, or 19 described above. For example, in some embodiments, system 10 may be configured as a sensing and/or monitoring system configured to measure atrial stretch based on hemodynamic parameters (as described herein, e.g., venous, pulmonary, and/or systemic hemodynamic parameters). In such embodiments, system 10 would not need pressure generator 14 for example, or the components which control pressure generation based on the sensor output signals. As another example, system 10 may include more than one sensor only for embodiments where one would like to measure delay/transfer times as described herein (e.g., two sensors are needed in such embodiments, one at the venous and one at the arterial side, with both being preload-dependent).

Returning to FIG. 1, processor 20 is configured to provide information processing capabilities in system 10. As such, processor 20 may comprise one or more of a digital processor, an analog processor, a digital circuit designed to process information, an analog circuit designed to process information, a state machine, and/or other mechanisms for electronically processing information. Although processor 20 is shown in FIG. 1 as a single entity, this is for illustrative purposes only. In some implementations, processor 20 may comprise a plurality of processing units. These processing units may be physically located within the same device (e.g., pressure generator 14), or processor 20 may represent processing functionality of a plurality of devices operating in coordination.

As shown in FIG. 1, processor 20 is configured to execute one or more computer program components. The one or more computer program components may comprise one or more of a ventilation parameter component 40, a control component 42, a hemodynamics component 44, an adjustment component 46, and/or other components. Processor 20 may be configured to execute components 40, 42, 44, and/or 46 by software; hardware; firmware; some combination of software, hardware, and/or firmware; and/or other mechanisms for configuring processing capabilities on processor 20.

It should be appreciated that although components 40, 42, 44, and 46 are illustrated in FIG. 1 as being co-located within a single processing unit, in implementations in which processor 20 comprises multiple processing units, one or more of components 40, 42, 44, and/or 46 may be located remotely from the other components. The description of the functionality provided by the different components 40, 42, 44, and/or 46 described below is for illustrative purposes, and is not intended to be limiting, as any of components 40, 42, 44, and/or 46 may provide more or less functionality than is described. For example, one or more of components 40, 42, 44, and/or 46 may be eliminated, and some or all of its functionality may be provided by other components 40, 42, 44, and/or 46. As another example, processor 20 may be configured to execute one or more additional components that may perform some or all of the functionality attributed below to one of components 40, 42, 44, and/or 46.

Ventilation parameter component 40 is configured to determine ventilation parameters of the pressure support therapy. The ventilation parameters are determined based on the output signals from sensors 17, 18, and/or 19, and/or other information. The parameters may comprise gas parameters related to the pressurized flow of breathable gas, breathing parameters related to the respiration of subject 12, and/or other parameters. The information determined by parameter component 40 may be used for controlling pressure generator 14, stored in electronic storage 24, and/or used for other uses. The one or more gas parameters of the pressurized flow of breathable gas may comprise, for example, one or more of a pressure, a flow rate, a volume, humidity, temperature, acceleration, velocity, a gas composition (e.g., a $CO_2$ composition) and/or other gas parameters. Breathing parameters related to the respiration of subject 12 may comprise a tidal volume, a timing (e.g., beginning and/or end of inhalation, beginning and/or end of exhalation, etc.), a respiration rate, a duration (e.g., of inhalation, of exhalation, of a single breathing cycle, etc.), respiration frequency, an indication of respiratory effort, and/or other breathing parameters.

Control component 42 is configured to control pressure generator 14 to generate the pressurized flow of breathable gas. Control component 42 is configured to cause pressure generator 14 to generate the pressurized flow of breathable gas in accordance with a pressure support therapy regime. Control component 42 is configured to cause pressure generator 14 to control the one or more ventilation parameters of the pressurized flow of breathable gas (e.g., described above) according to the prescribed pressure support therapy regime. Control component 42 is configured to control pressure generator 14 based on information related to the output signals from sensors 17, 18, and/or 19, information determined by ventilation parameter component 40, information determined by hemodynamics component 44 (described below), information determined by adjustment component 46 (described below), information entered and/or selected by a user via user interface 22, and/or other information. The pressurized flow of breathable gas generated by pressure generator 14 is controlled to facilitate pulmonary and systemic circulation in subject 12 (e.g., as described below). In some embodiments, control component 40 may be configured to control pressure generator 14 to generate the flow of gas in accordance with a ventilation therapy regime, a positive airway pressure support therapy regime, and/or other pressure support therapy regimes. By way of non-limiting example, control component 40 may control pressure generator 14 such that the pressure support provided to subject 12 via the flow of gas comprises continuous positive airway pressure support (variable CPAP), bi-level positive airway pressure support (BPAP), low pressure positive airway pressure (lpPAP) therapy, high pressure positive airway pressure (hpPAP) therapy, and/or other types of pressure support therapy. In some embodiments, control component 42 may be configured to control the pressurized flow of breathable gas based on the information described above differently for spontaneously breathing subjects relative to subjects who require assisted ventilation.

Hemodynamics component 44 is configured to determine hemodynamic parameters in subject 12. The hemodynamic parameters are determined based on the information from sensors 17, 18, and/or 19, and/or based on other information. Hemodynamic parameters comprise parameters related to heart function, pulmonary circulation, systemic circulation, and/or other physiological functions. For example, hemodynamic parameters may include heart rate, blood pressure, blood gas quantities and/or composition, parameters related to cardiac afterload, a transpulmonary delay/transfer time (e.g., described herein), parameters related to an amount of accumulated blood at one or more locations in the circulatory system, parameters related to overloading one or both sides of the heart, parameters related to atrial fibrillation, and/or other parameters. In some embodiments, hemodynamics component 44 is configured to determine "venous" parameters (e.g., pulsations and/or other parameters). In some embodiments, hemodynamics component 44 is configured to determine "preload-dependent" parameters (e.g., pulse pressure, stroke volume, "arterial" and/or "venous" PPG, etc.). For example, as described herein, the preload is controlled to prevent atrial fibrillation.

In some embodiments, based on such parameters, hemodynamics component 44 is configured to determine whether an overload of the right and/or left atrium of subject 12 has occurred, whether an episode of atrial fibrillation is occurring or is likely to occur in subject 12, and/or determine other physiological conditions. The right atrial overloading, the increased right atrial preload can be extracted from the respiration induced modulation of the venous accumulation sensed by sensor 18. An increase of the respiration induced modulation is specific for an increased right atrial preload and consequently an increased afterload of the right ventricle causing an increase of the accumulated blood in the pulmonary arteries and an increase of the pulmonary arterial pressure. The increased preload of the left atrium can be sensed by sensor 19. The transfer time, the delay time of the respiration induced modulation of the blood wave flowing through the pulmonary arteries and veins is specific for the accumulated blood, the blood pressure, the left atrial preload and the left ventricular afterload. An increase of the blood pressure in the pulmonary circulation causes an increase of the pulse transit time in the pulmonary vessels consequently causing a decreased delay time sensed by sensor 18 and 19. A left atrial preload change corresponds linearly to a change of the left ventricular afterload. Preload changes at the left atrium and the delay time through the pulmonary circulation are reciprocally correlated. A decline of the delay time is an indication for an increased preload. Persistently increased preload is the cause for atrial overloading, stretching of atrial chamber walls, cardiac remodeling. All are primary causes in the onset of paroxysmal atrial fibrillation.

In some embodiments, hemodynamics component 44 is configured to determine whether an episode of atrial fibrillation is occurring or is likely to occur based on the information in the output signals from sensors 17, 18, and/or 19, and/or other information. In some embodiments, determining whether an episode of atrial fibrillation is occurring or is likely to occur in subject 12 includes determining the heart rate (e.g., via the output signals of sensor 19) and/or respiration rate (e.g., via the output signals of sensor 17 and/or based on information determined by parameter component 40), comparing the heart rate and/or respiration rate to a threshold value, and determining that atrial fibrillation is occurring and/or is likely to occur responsive to the heart rate and/or respiration rate breaching the threshold. For example, hemodynamics component 44 may determine that atrial fibrillation is occurring or is about to occur responsive to the heart rate and/or respiration rate slowing to a rate that is below a fibrillation threshold level. The fibrillation threshold level may be programmed at manufacture, input and/or adjusted by a user via user interface 22, and/or determined in other ways.

In some embodiments, prediction of an episode of atrial fibrillation is based on how frequent atrial extra-systoles occur. When the number of atrial extra-systoles per time unit exceeds a certain threshold, atrial fibrillation is likely to occur when no intervention would take place. This could therefore be a trigger to change the pressure control of the ventilation support system. Atrial extra-systoles can be measured with for example ECG electrodes or with a blood volume or blood velocity sensor, which could use a technique such as PPG, laser speckle or ultrasound.

In some embodiments, changes in AC value, DC value, or features of waveform morphology of blood volume sensors (like PPG) are used to determine whether an episode of atrial fibrillation is occurring or is likely to occur.

In some embodiments changes in the heart rate, breathing rate, or the detection of extra systoles are used to change the ventilation settings to determine the hemodynamic response with respect to a change of heart rate, breathing rate and the data sensed by sensor 18 and sensor 19.

In some embodiments, determining whether an episode of atrial fibrillation is occurring or is likely to occur in subject 12 includes determining whether increased blood accumulation/volume overloading is present in the pulmonary vessels. In some embodiments, determining whether increased blood accumulation/volume overloading is present in the pulmonary vessels comprises determining a transpulmonary delay/transfer time of increased blood flow (e.g., a blood wave) in the pulmonary circulation system of subject 12. As described above, the delay/transfer time (e.g., the delay time measured by sensor 18 and 19) corresponds to an amount of accumulated blood in a right atrium, pulmonary veins, and left atrium of subject 12. In this context delay/transfer/transit time is defined as the time a volumetric change in the right atrial preload takes before a volumetric change in the afterload of the left ventricle (change in LV stroke volume) can be measured.

Changes in the transfer time correspond to changes in the amount of accumulated blood. For example, a reduction of the pulmonary transfer time correlates with an increase of the pulse wave velocity. The pulse wave velocity correlates with the pressure in the vessels which is an indirect measure of the amount of accumulated blood. In some embodiments, hemodynamics component 44 is configured to determine correlations between therapy pressures, pulsation and/or dilation, and the arrival and/or transfer time of blood waves for subject 12.

Figure 5A:
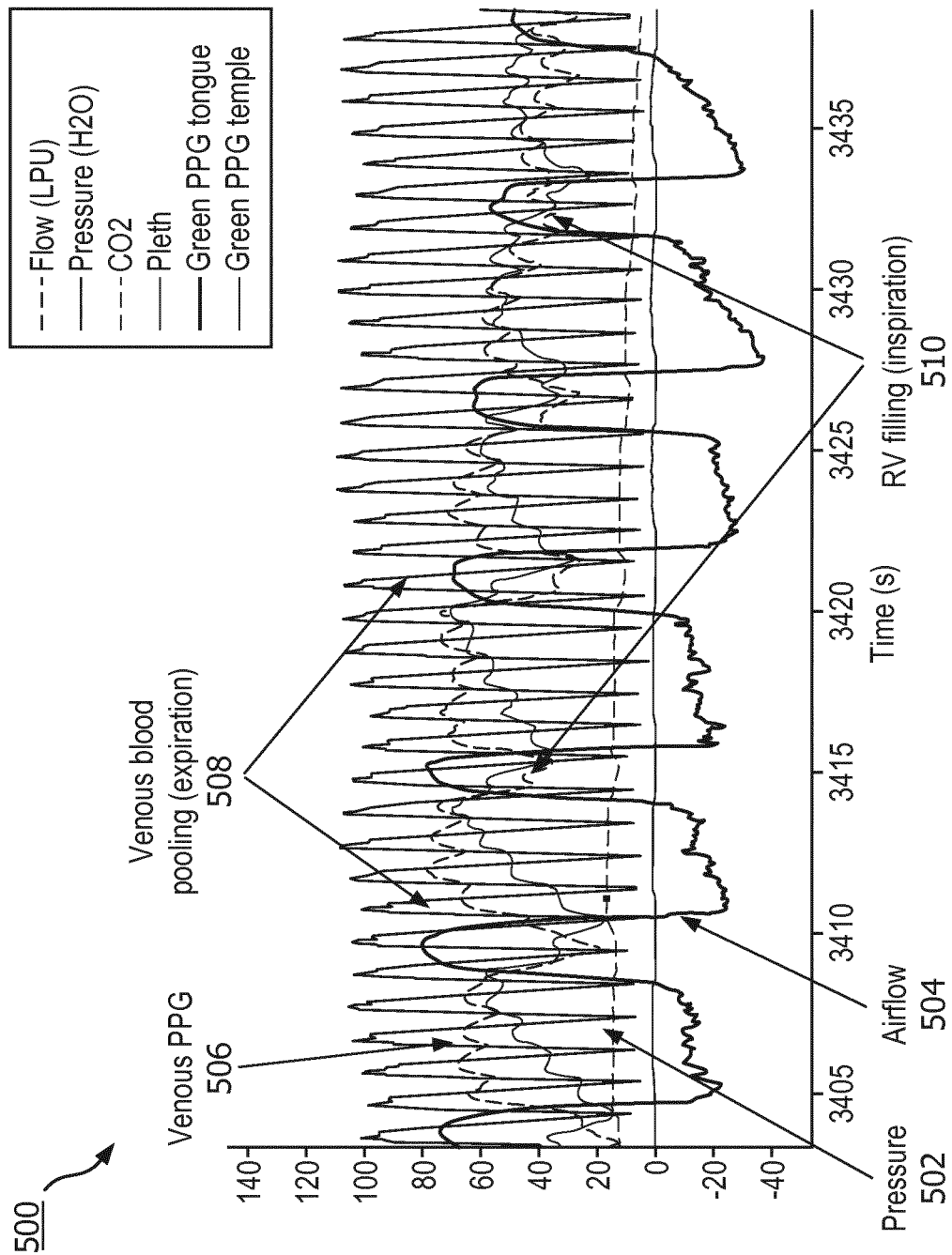
FIG. 5A is a graphical representation of information conveyed by one or more output signals generated by the system, and/or parameters determined by the system.

FIG. 5A is a graphical representation 500 of information conveyed by one or more output signals generated by system 10 (FIG. 1), and/or parameters determined by system 10. For example, FIG. 5A illustrates airway pressure 502, airflow (flow rate) 504, venous PPG 506, venous blood pooling (during expiration) 508, and right ventricle filling (during inspiration) 510. In some embodiments, system 10 may determine one or more of the parameters based on the graphical representation itself.

Figure 5B:
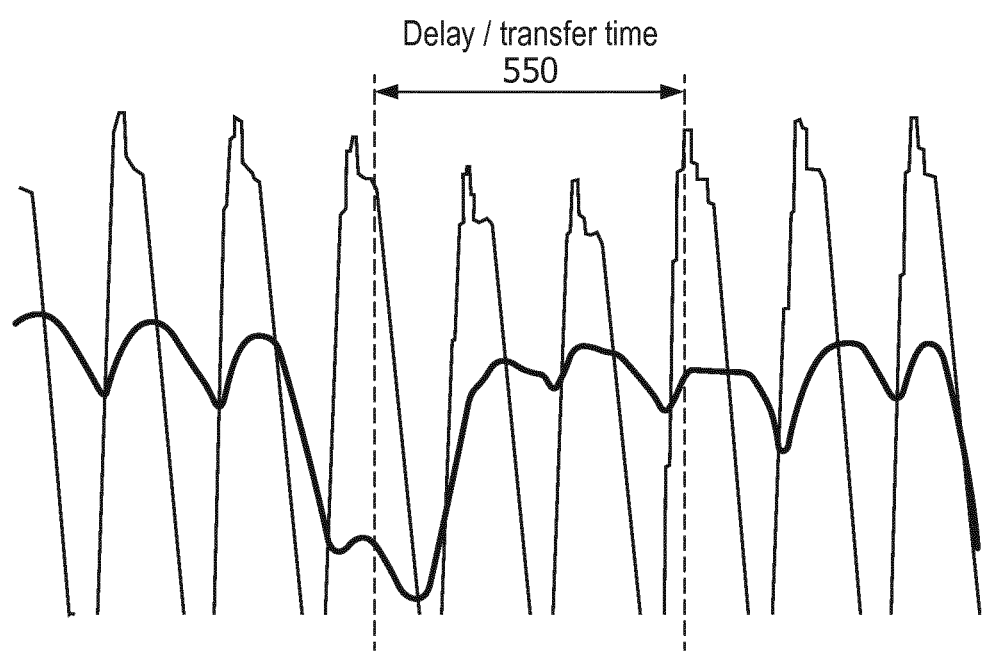
FIG. 5B illustrates a delay/transfer time.

FIG. 5B (a zoomed in portion of FIG. 5A) illustrates a delay/transfer time 550. As described above, delay/transfer time 550 may be a surrogate representative of the accumulated blood in the right atrium, the pulmonary veins, and the left atrium of subject 12. Delay/transfer time 550 is measured and determined by the time delay of the respiration-induced modulation in the signal of sensor 18 (FIG. 1) compared with the modulated signal of sensor 19 (FIG. 1). In some embodiments, delay/transfer time 550 is the time delay of the respiration-induced modulation in the signal of sensor 18 compared with the air flow measured by the ventilator. In some embodiments, delay/transfer time 550 is the time delay of the respiration-induced modulation in the signal of sensor 19 compared with the air flow measured by the ventilator. In some embodiments, the delay/transfer time may comprise a time difference between a minimum in the signal of sensor 18 and a maximum in the signal of sensor 19, for example. In some embodiments, determining the delay/transfer time between sensor 19 and sensor 18 is the same as and/or similar to determining the delay/transfer time between sensor 19 and the flow signal of the ventilator, so that no sublingual sensor would be needed in such embodiments. In some embodiments, delay/transfer time 550 is the determined based on the pulse arrival times and pulse transit times of the pressure wave of: the ECG versus the pulse signal of sensor 18, the ECG versus the pulse signal of sensor 19, the pulse signal of sensor 18 versus that of sensor 19, and/or other delay/transfer times.

Returning to FIG. 1, adjustment component 46 is configured to cause pressure generator 14 to adjust the one or more ventilation parameters of the pressurized flow of breathable gas based on the information determined by hemodynamics component 44, the information from sensors 17, 18, and/or 19, and/or other information. Adjustment component 46 is configured to control pressure generator 14 to adjust the pressure levels and/or other parameters of the pressurized flow of breathable gas during inhalation and/or exhalation by subject 12 to facilitate pulmonary and systemic circulation. In some embodiments, adjustment component 46 is configured to cause adjustment of the pressure levels of the pressurized flow of breathable gas during one or both of inhalation and exhalation by amounts that correspond to an amount of venous blood accumulation during cardiac preload and/or an amount of cardiac hypervolemic stress in subject 12. In some embodiments, adjustment component 46 is configured to cause pressure generator 14 to adjust the ventilation parameters of the pressurized flow of breathable gas via electronic communication with the valves, blower, motor (e.g., the servo controllers, valves, motors), and/or other components of pressure generator 14.

For example, adjustment component 46 may cause pressure generator 14 to operate in an lpPAP and/or hpPAP therapy mode, and/or switch from operating in a typical CPAP (or some other typical therapy mode) to the lpPAP and/or hpPAP therapy modes. Adjustment component 46 may be configured such that therapy parameters of the lpPAP and/or hpPAP therapy discourage and/or prevent volume overloading, and decrease the amount of accumulated blood in the atria. During typical CPAP (for example), as long as the CPAP pressure is not higher than a given threshold level (e.g., which is subject dependent but usually about 4 cmH20), exhalation by subject 12 may be passive, with little to no muscular effort needed to assist the outflow because the natural recoil of the ribcage and alveoli are enough to overcome the CPAP pressure. If the CPAP exhalation pressure is higher than a given threshold level (e.g., something above the 4 cmH20, usually about 8 cmH20) exhalation requires muscular effort by subject 12 (the amount of muscular effort required by individual subjects 12 varies across the range of 4-8 cmH20).

Controlling pressure generator 14 to operate in an lpPAP therapy mode assists the heart during the inhalation cycle. Adjustment component 46 is configured to adjust the pressure levels and/or the parameters of the lpPAP therapy such that during inhalation the pressurized flow of breathable gas is provided at a pressure level that is higher than the pressure level specified by the pressure support therapy regime (e.g., typical CPAP pressure support therapy), and exhalation by subject 12 remains a passive expiratory airflow without need of muscular effort by subject 12 to exhale. In some embodiments, lpPAP therapy increases (e.g., makes less negative) the intrathoracic pressure during inhalation, which reduces the venous return from the systemic veins, and lowers the preload of the right atrium. In some embodiments, lpPAP therapy increases the external positive end-expiratory pressure (ePEEP), which increases the vascular resistance of the intra-alveolar capillaries to lower the trans-alveolar perfusion, and lowers the preload of the left atrium.

Controlling pressure generator 14 to operate in an hpPAP therapy mode includes assisting the heart during the inhalation cycle as described above using lpPAP therapy. Adjustment component 46 is configured such that hpPAP therapy additionally causes pressure generator 14 to generate the pressurized flow of breathable gas during exhalation at a pressure level that is higher than the pressure level provided during inhalation. At this higher expiratory pressure level, the recoil behavior of the alveoli and the ribcage is not sufficient for subject 12 to naturally and/or involuntarily complete the expiratory tidal airflow. Instead, subject 12 must breathe out actively against the provided exhalation pressure using muscular expiratory breathing effort. This breathing effort during exhalation acts as an expiratory pulmonary muscle pump. In some embodiments, the hpPAP therapy rapidly increases (e.g., makes less negative after inhalation) the intrathoracic pressure to further lower the preload of the right atrium. In some embodiments, the hpPAP therapy increases the transmural pressure on the extra-alveolar vessels during exhalation to assist an increased trans-alveolar perfusion pressure to increase the alveolar blood flow.

It should be noted that the pressure levels and/or other parameters of the lpPAP and/or hpPAP therapies are specific to subject 12. The pressure levels and/or other parameters may be determined at manufacture, set and/or adjusted by a physician and/or other caregivers (e.g., via user interface 22), determined based on (integrated) electromyography (EMG) and/or other methods, and/or determined in other ways.

Figure 6:
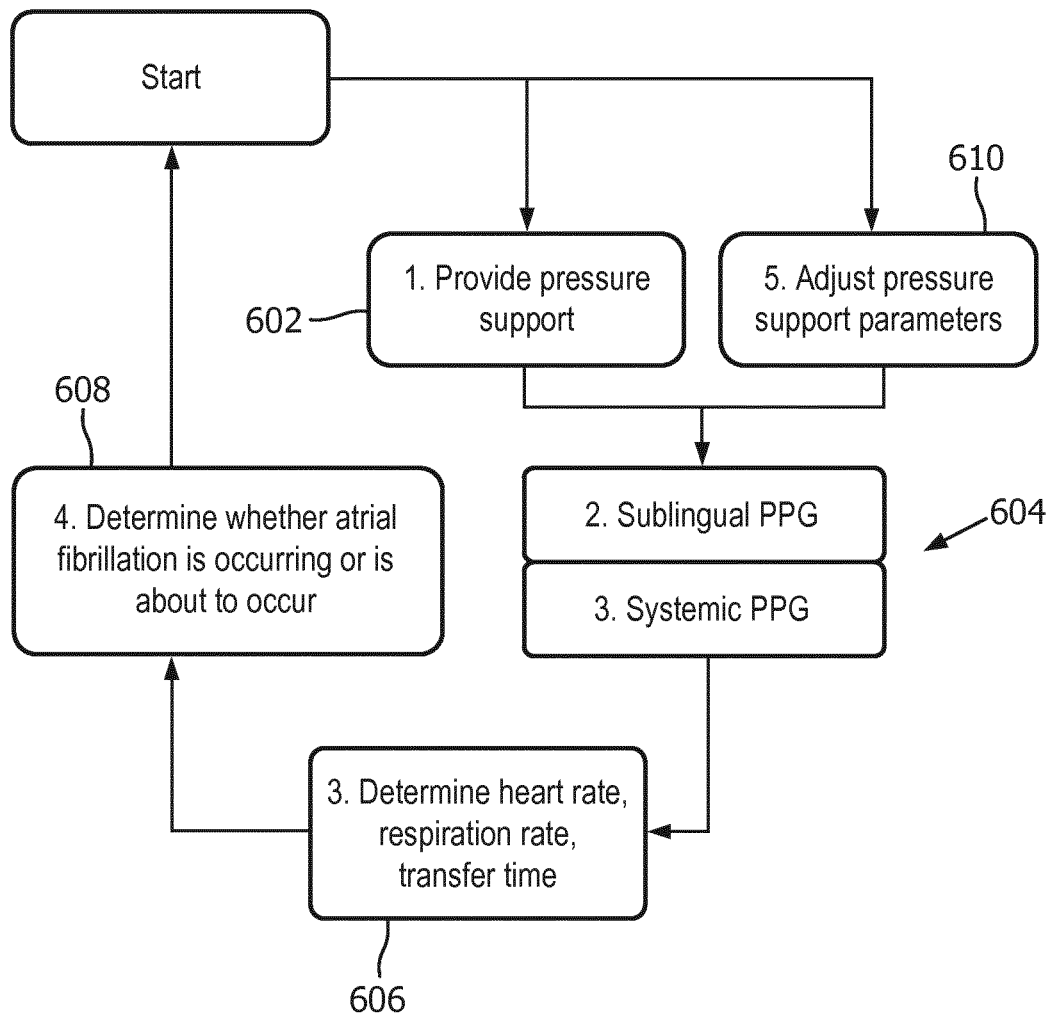
FIG. 6 illustrates adjusting exhalation and/or inhalation pressure levels of pressure support therapy responsive to a determination that atrial fibrillation is occurring or is likely to occur.

In some embodiments, responsive to a determination that atrial fibrillation is occurring or is likely to occur by hemodynamics component 44, adjustment component 46 is configured to control pressure generator 14 to adjust the pressure levels during one or both of inhalation and exhalation to facilitate the pulmonary and systemic circulation, and discourage or prevent the episode of atrial fibrillation. For example, FIG. 6 illustrates adjusting the exhalation and/or inhalation pressure levels of the pressure support therapy responsive to a determination that atrial fibrillation is occurring or is likely to occur. As shown in FIG. 6, pressure support is provided 602 to a subject (not shown in FIG. 6). Sublingual and/or systemic PPG sensors generate 604 output signals conveying information used to determine 606 the heart rate of the subject, the respiration rate of the subject, a transfer time (e.g., as described above), and/or other parameters. The heart rate, respiration rate, transfer time, and/or other parameters are compared 608 to corresponding threshold values to determine whether atrial fibrillation is occurring and/or is likely to occur (e.g., responsive to the heart rate, respiration rate, transfer time, etc., breaching a threshold). Parameters (e.g., an exhalation pressure level) of the pressure support are adjusted 610 responsive to a determination that atrial fibrillation is occurring or is likely to occur.

Returning to FIG. 1, in some embodiments, responsive to determining that an overload of the right atrium in subject 12 has occurred (e.g., based on the transfer time and/or other information), adjustment component 46 is configured to cause pressure generator 14 to increase the pressure level during inhalation above the level indicated by the pressure support therapy regime (e.g., a typical CPAP therapy regime) and cause oscillation of the pressure about the increased pressure level with a timing that corresponds to systolic and diastolic phases of a cardiac cycle in subject 12 (e.g., lpPAP).

Responsive to determining that an overload of the left atrium has occurred, adjustment component 46 is configured to cause pressure generator 14 to adjust the pressure levels during inhalation and exhalation such that the pressure level during exhalation is higher than the pressure level during inhalation (e.g., hpPAP). Adjustment component 46 is configured to cause pressure generator to oscillate the pressure about the adjusted pressure levels during inhalation and exhalation with an oscillation amplitude that is larger during exhalation than inhalation, and with an oscillation timing that corresponds to the systolic and diastolic phases of the cardiac cycle in subject 12.

Figure 7:
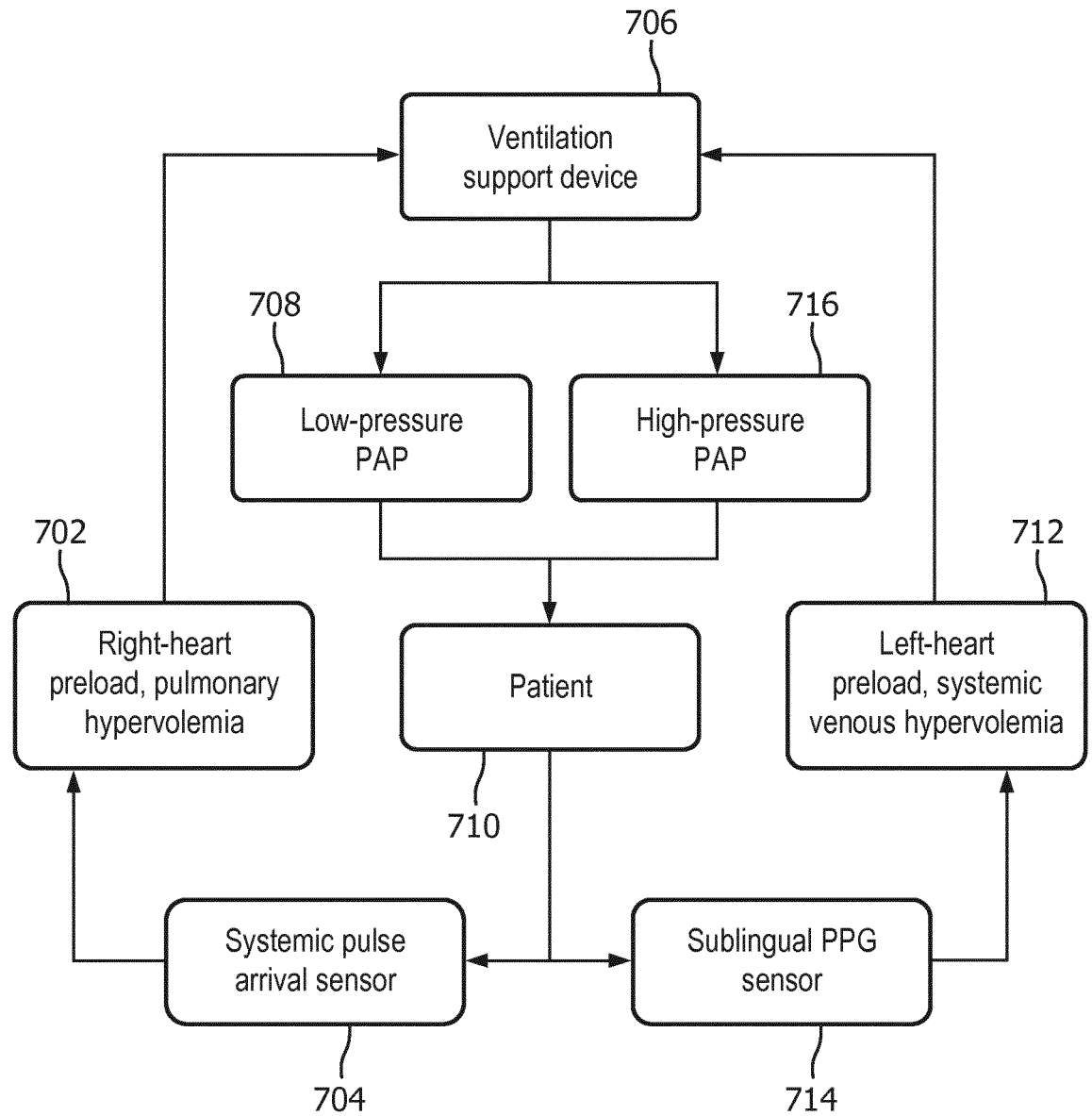
FIG. 7 illustrates determining whether the right and/or left atrium in the subject are overloaded and adjusting the pressure support therapy based on such a determination.

Determining whether the right and/or left atrium in subject 12 is overloaded and then adjusting the pressure support therapy based on such a determination is illustrated in FIG. 7. As shown in FIG. 7, responsive to a determination that the right atrium is overloaded (right heart preload, blood volume overloading) 702 based on information from a systemic pulse arrival sensor (e.g., comprising sensors 18 and 19 shown in FIG. 1) 704 and/or other information, a ventilation support device (e.g., pressure generator 14) 706 is controlled to generate lpPAP 708 for a patient (e.g., subject 12) 710. Responsive to a determination that the left atrium is overloaded (left heart preload, systemic venous blood volume overloading) 712 based on information from a sublingual PPG sensor (e.g., sensor 18) 714 and/or other information, ventilation support device 706 is controlled to generate hpPAP 716 for patient 710.

Figure 8:
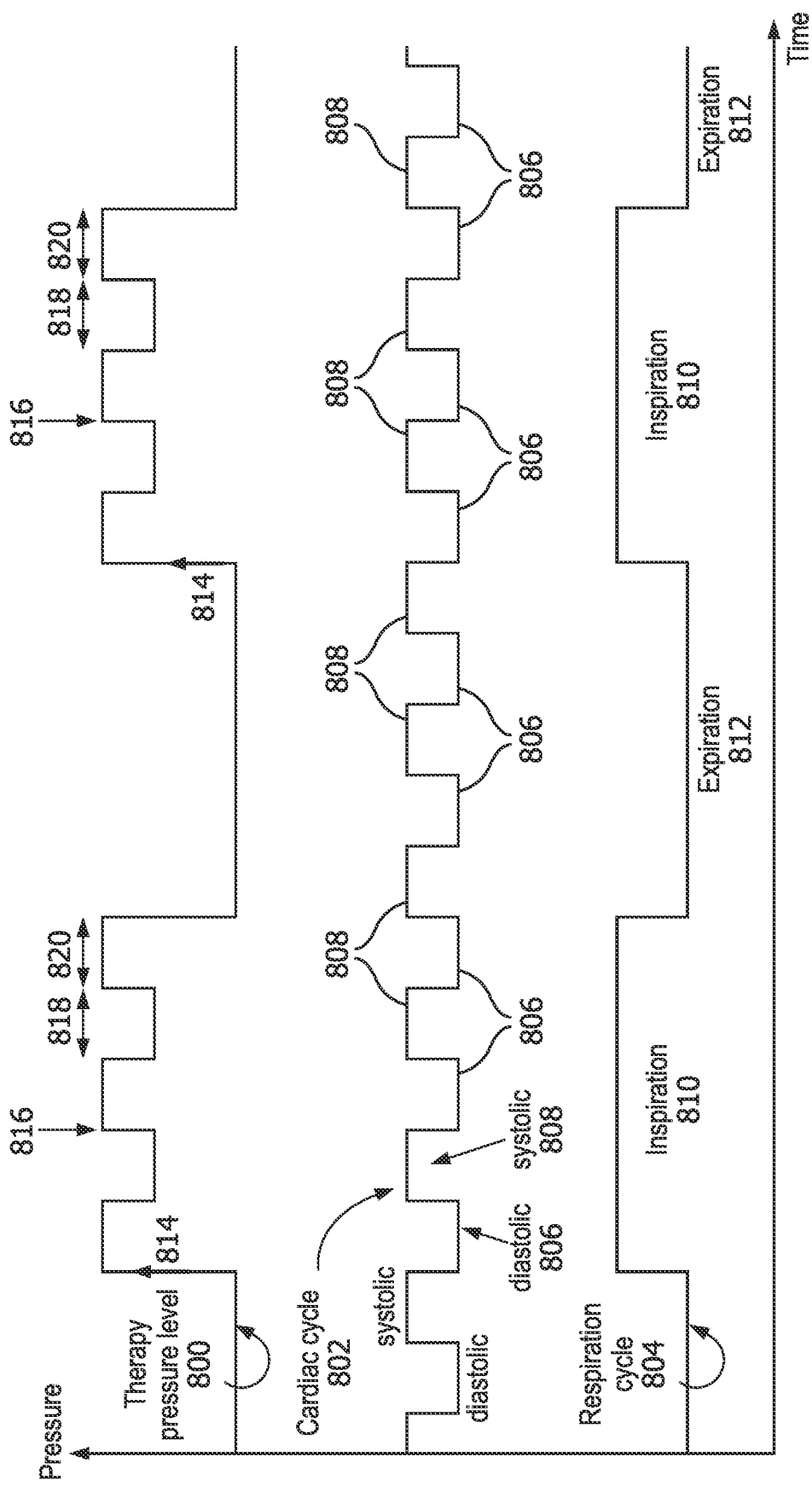
FIG. 8 illustrates a pressure level profile of pressure support provided to the subject responsive to determining that an overload of the right atrium in the subject has occurred.

FIG. 8 illustrates a pressure level profile 800 of pressure support provided to subject 12 (FIG. 1) responsive to determining that an overload of the right atrium in subject 12 has occurred. Pressure level profile 800 is shown relative to diastolic 806 and systolic 808 phases of the cardiac cycle 802 and inspiration 810 and expiration 812 phases of the respiration cycle 804. As shown in FIG. 8, responsive to a determination that an overload of the right atrium has occurred, the pressure level is increased 814 during inspiration above the level indicated by the pressure support therapy regime (e.g., a typical CPAP therapy regime) and caused to oscillate 816 about the increased pressure level with a timing 818, 820 that corresponds to systolic and diastolic phases of cardiac cycle 802.

Figure 9:
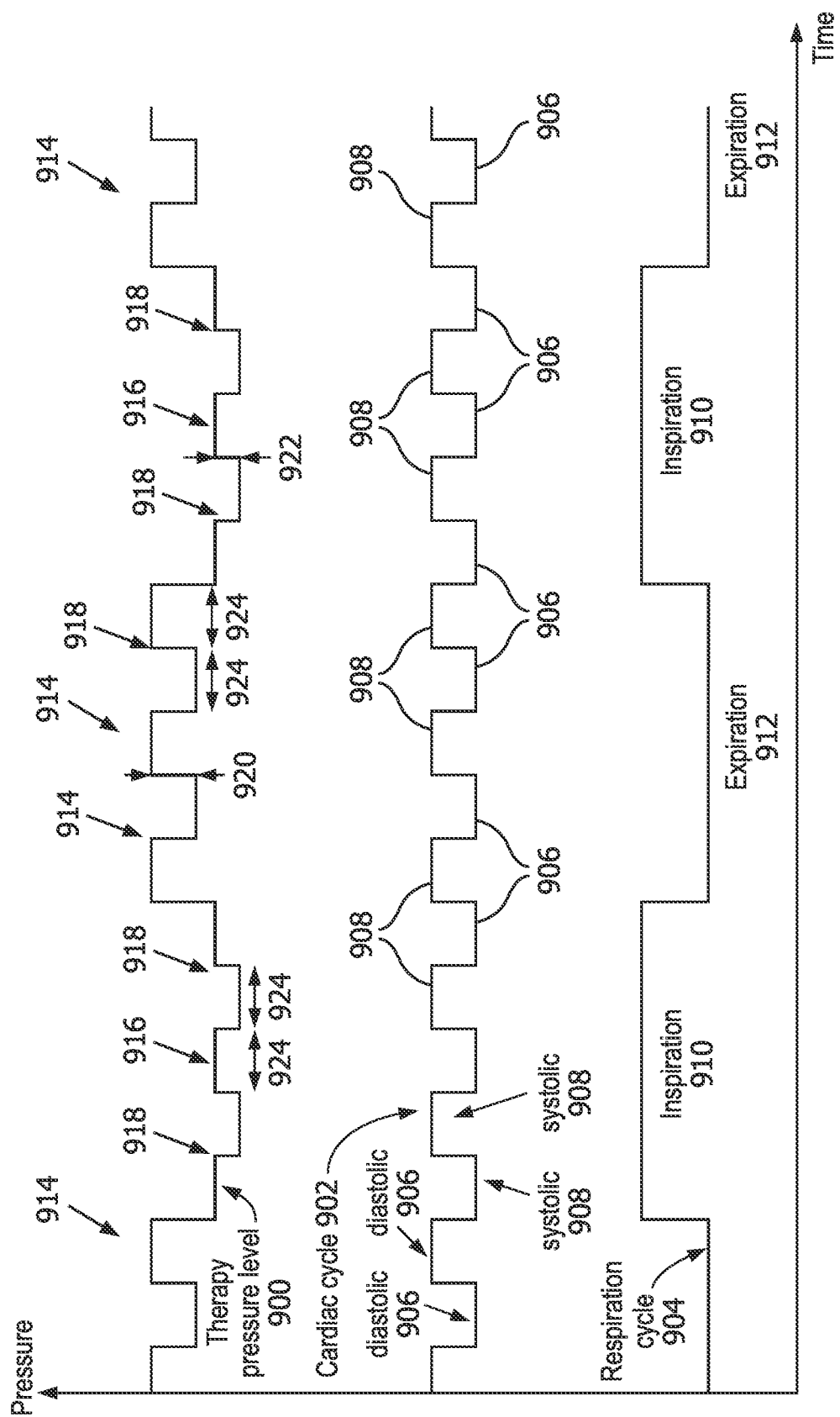
FIG. 9 illustrates a pressure level profile of pressure support provided to the subject responsive to determining that an overload of the left atrium in the subject has occurred.

FIG. 9 illustrates a pressure level profile 900 of pressure support provided to the subject (e.g., subject 12 shown in FIG. 1) responsive to determining that an overload of the left atrium in the subject has occurred. Pressure level profile 900 is shown relative to diastolic 906 and systolic 908 phases of the cardiac cycle 902 and inspiration 910 and expiration 912 phases of the respiration cycle 904. As shown in FIG. 9, responsive to a determination that an overload of the left atrium has occurred, the pressure level is adjusted such that the pressure level during expiration 914 is higher than the pressure level during inspiration 916. In addition, the pressure level oscillates 918 about the adjusted pressure levels during inhalation and exhalation with an oscillation amplitude 920, 922 that is larger 920 during expiration than the amplitude during inspiration 922, and with an oscillation timing 924 that corresponds to the systolic and diastolic phases of the cardiac cycle in the subject.

Returning to FIG. 1, by way of a non-limiting example of the operation of system 10, optical PPG sensor 18 may be located at a branch of the internal jugular vein in subject 12 and monitor the respiration related venous blood pooling and filling of the right atrium. Parameter component 40 and/or hemodynamics component 44 may determine the pulse rate and the respiration rate based on the information from sensors 17, 18, and/or 19. A signal amplitude (e.g., from sensor 18) may be representative of the effort of the heart during respiration and the dilatation of the vein, which corresponds to the blood accumulation. If the amplitude of the signal is outside of a predetermined range for subject 12, the therapy pressure level may be increased for the inspiration cycle. Subject 12 may respond autonomously by decreasing the muscular effort needed for breathing. The response to the decreased effort may be determined based on a change of the amplitude of the signal from sensor 18 at the sublingual vein in the next breathing cycle. Information from sensor 19 may be used to determine a change in the transfer time accordingly.

By way of a second non-limiting example of the operation of system 10, hemodynamics component 44 is configured to detect increases in the transfer times of blood waves and determine that volume overloading in the pulmonary system occurs (e.g., as described above). This overloading is a typical symptom in patients with congestive heart failure (CHF). The increased transfer times correlate with the amount of accumulated blood in the capacitive, highly compliant, pulmonary vessels. In such embodiments, adjustment component 46 is configured to control pressure generator 14 to increase the therapy pressure level during expiration to a level that requires an active muscular effort during expiration by subject 12. The increased pressure level causes an increase in the vascular resistance of the intra-alveolar capillaries, so less blood is flowing into the pulmonary veins, and the increased transmural pressure at the pulmonary veins (extra-alveolar veins) increases the preload of the left side of the heart. Both effects contribute to balancing the pulmonary circulation such that the blood accumulated in the pulmonary circulation system is decreased (e.g., as evidenced in a decrease of the pulmonary transfer time determined by hemodynamics component 44).

Returning to FIG. 1, user interface 22 is configured to provide an interface between system 10 and subject 12 and/or other users through which subject 12 and/or other users provide information to and receive information from system 10. For example, user interface 22 is configured to receive entry and/or selection of control inputs from subject 12 and/or other users that specify control parameters for the pressure support therapy and/or other information. Other users may comprise a caregiver, a doctor, a decision maker, and/or other users. User interface 22 enables data, cues, results, and/or instructions and any other communicable items, collectively referred to as "information," to be communicated between a user (e.g., subject 12) and one or more of pressure generator 14, sensors 17, 18, 19, processor 20, electronic storage 24, and/or other components of system 10. Examples of interface devices suitable for inclusion in user interface 22 comprise a keypad, buttons, switches, a keyboard, knobs, levers, a display screen, a touch screen, speakers, a microphone, an indicator light, an audible alarm, a printer, a tactile feedback device, and/or other interface devices. In some embodiments, user interface 22 comprises a plurality of separate interfaces. In some embodiments, user interface 22 comprises at least one interface that is provided integrally with pressure generator 14.

It is to be understood that other communication techniques, either hard-wired or wireless, are also contemplated by the present disclosure as user interface 22. For example, the present disclosure contemplates that user interface 22 may be integrated with a removable storage interface provided by electronic storage 24. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 22 comprise, but are not limited to, an RS-232 port, RF link, an IR link, modem (telephone, cable or other). In short, any technique for communicating information with system 10 is contemplated by the present disclosure as user interface 22.

In some embodiments, electronic storage 24 comprises electronic storage media that electronically stores information. The electronic storage media of electronic storage 24 may comprise system storage that is provided integrally (i.e., substantially non-removable) with system 10; removable storage that is removably connectable to system 10 via, for example, a port (e.g., a USB port, a firewire port, etc.) or a drive (e.g., a disk drive, etc.); remotely located electronic (e.g., "cloud") storage wirelessly accessed by system 10; and/or other electronic storage. Electronic storage 24 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), and/or other electronically readable storage media. Electronic storage 24 may store software algorithms, information determined by processor 20, information received via user interface 22, and/or other information that enables system 10 to function as described herein. Electronic storage 24 may be (in whole or in part) a separate component within system 10, or electronic storage 24 may be provided (in whole or in part) integrally with one or more other components of system 10 (e.g., user interface 22, processor 20, etc.).

Figure 10:
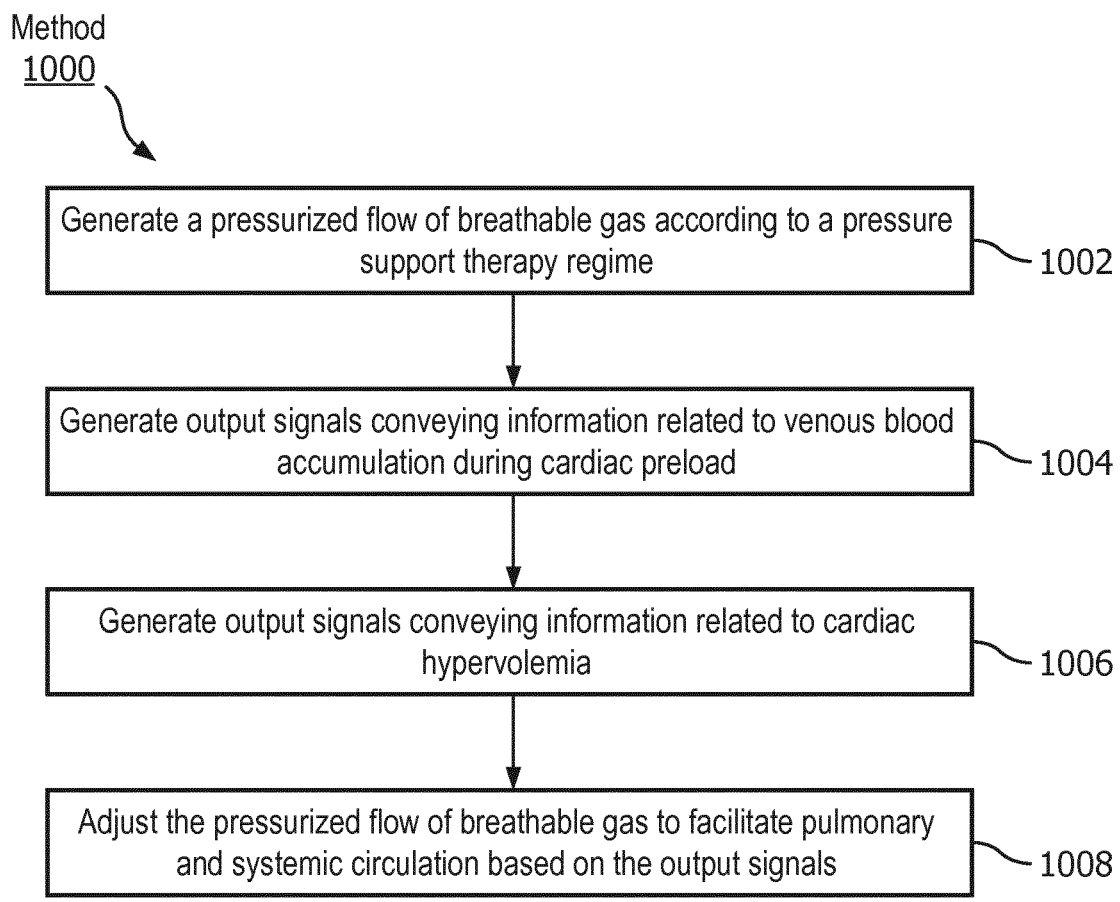
FIG. 10 illustrates a method for facilitating pulmonary and systemic circulation in the subject with a ventilation support system.

FIG. 10 illustrates a method 1000 for facilitating pulmonary and systemic circulation in the subject with a ventilation support system. The system comprises a pressure generator, a first sensor, a second sensor, one or more hardware processors, and/or other components. The one or more hardware processors are configured by machine readable instructions to execute computer program components. The computer program components include a control component, a hemodynamics component, an adjustment component, and/or other components. The operations of method 1000 presented below are intended to be illustrative. In some embodiments, method 1000 may be accomplished with one or more additional operations not described, and/or without one or more of the operations discussed. Additionally, the order in which the operations of method 1000 are illustrated in FIG. 10 and described below is not intended to be limiting.

In some embodiments, method 1000 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 1000 in response to instructions stored electronically on an electronic storage medium. The one or more processing devices may include one or more devices configured through hardware, firmware, and/or software to be specifically designed for execution of one or more of the operations of method 1000.

At an operation 1002, a pressurized flow of breathable gas is generated according to a pressure support therapy regime. The pressure support therapy regime indicates pressure levels of the pressurized flow of breathable gas provided by the pressure generator during inhalation and exhalation by the subject. In some embodiments, operation 1002 is performed by a pressure generator the same as or similar to pressure generator 14 (shown in FIG. 1 and described herein).

At an operation 1004, output signals conveying information related to venous blood accumulation during cardia preload are generated. In some embodiments the output signals are generated by a sublingual photoplethysmography (PPG) sensor configured to generate output signals that convey information related to a pulsation of a sublingual vein modulated by a respiration cycle of the subject. In some embodiments, operation 1004 is performed by a sensor the same as or similar to sensor 18 (shown in FIG. 1 and described herein).

At an operation 1006, output signals conveying information related to cardiac blood volume overloading are generated. In some embodiments, the output signals are generated by a systemic PPG sensor configured to removably couple with a forehead, temple, ear, or finger of the subject. In some embodiments, operation 1006 is performed by a sensor the same as or similar to sensor 19 (shown in FIG. 1 and described herein).

At an operation 1008, the pressurized flow of breathable gas is adjusted, based on the output signals, to facilitate pulmonary and systemic circulation. In some embodiments, the pressure generator is controlled to adjust the pressure levels of the pressurized flow of breathable gas during one or both of inhalation and exhalation. In some embodiments, causing the pressure generator to adjust the pressure levels of the pressurized flow of breathable gas comprising adjusting the pressure levels by amounts that correspond to an amount of venous blood accumulation during cardiac preload and/or an amount of cardiac hypervolemic stress in the subject. In some embodiments, operation 1008 is performed by a processor component the same as or similar to adjustment component 46 (shown in FIG. 1 and described herein).

In some embodiments, method 1000 includes determining, with the hemodynamics component of the one or more hardware processors, based on the output signals from the first sensor and the second sensor, whether an episode of atrial fibrillation is occurring or is likely to occur in the subject; and responsive to a determination that atrial fibrillation is occurring or is likely to occur, controlling, with the adjustment component of the one or more hardware processors, the pressure generator to adjust the pressure levels during one or both of inhalation and exhalation to facilitate the pulmonary and systemic circulation, and discourage or prevent the episode of atrial fibrillation. In some embodiments, determining whether an episode of atrial fibrillation is occurring or is likely to occur includes determining a transpulmonary transfer time of a blood wave in a pulmonary circulation system of the subject. The transfer time corresponds to an amount of accumulated blood in a right atrium, pulmonary veins, and left atrium of the subject.

In some embodiments, method 1000 includes determining, with the hemodynamics component of the one or more hardware processors, based on the output signals of the first sensor and the second sensor, whether an overload of a right and/or left atrium of the subject has occurred. In such embodiments, method 1000 further comprises, responsive to determining that an overload of the right atrium has occurred, causing, with the adjustment component of the one or more hardware processors, the pressure generator to increase the pressure level during inhalation above the level indicated by the pressure support therapy regime and cause oscillation of the pressure about the increased pressure level with a timing that corresponds to systolic and diastolic phases of a cardiac cycle in the subject. In such embodiments, method 1000 further comprises, responsive to determining that an overload of the left atrium has occurred, causing, with the adjustment component of the one or more hardware processors, the pressure generator to: adjust the pressure levels during inhalation and exhalation such that the pressure level during exhalation is higher than the pressure level during inhalation; and oscillate the pressure about the adjusted pressure levels during inhalation and exhalation with an oscillation amplitude that is larger during exhalation than inhalation, and with an oscillation timing that corresponds to the systolic and diastolic phases of the cardiac cycle.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

What is claimed is:

1. A sensing and monitoring system configured to measure atrial stretch in a subject based on one or more hemodynamic parameters, the system comprising:
    one or more external photoplethysmography (PPG) sensors configured to generate output signals, during ventilation of the subject, conveying information related to hemodynamic activity in the subject; and
    one or more hardware processors configured by machine-readable instructions to:
        determine the one or more hemodynamic parameters based on the output signals;
        determine a change in the atrial stretch indicative of an overload of a right and/or left atrium in the subject during ventilation based on the on the one or more determined hemodynamic parameters; and
        provide an output for adjusting, based on a determination that an overload of the right and/or left atrium of the subject has occurred, ventilation pressure provided to the subject by a ventilation support system.

2. The system of claim 1, wherein:
    wherein the one or more external PPG sensors comprise:
        a first PPG sensor configured to obtain data at a first location on the subject and a second PPG sensor configured to obtain data at a second location on the subject, the second location differing from the first location;
    the one or more hemodynamic parameters comprise atrial extra systoles determined based on output signals from the one or more external PPG sensors;
    responsive to detection of an atrial extra systole, the one or more hardware processors trigger a pressure generator to provide ventilation support to the subject; and
    the one or more hardware processors validate success of the ventilation support based on output signals from the one or more external PPG sensors that indicate reversion of overloading and/or atrial stretch in the subject.

3. The system of claim 1, further comprising a pressure generator that is part of the ventilation support system, the pressure generator configured to generate a pressurized flow of breathable gas for delivery to an airway of the subject according to a pressure support therapy regime, the pressure support therapy regime indicating pressure levels of the pressurized flow of breathable gas provided by the pressure generator during inhalation and exhalation by the subject;
    wherein the one or more external PPG sensors comprise:
        a first PPG sensor configured to obtain data at a first location on the subject and a second PPG sensor configured to obtain data at a second location on the subject, the second location differing from the first location;
    wherein the first PPG sensor is configured to generate output signals conveying information related to venous blood accumulation during cardiac preload in the subject; and
    the second PPG sensor is configured to generate output signals conveying information related to heart activity and/or systemic arterial circulation in the subject; and
    wherein the one or more hardware processors are configured to control the pressure generator to adjust the pressure levels of the pressurized flow of breathable gas during one or both of inhalation and exhalation to facilitate the pulmonary and systemic circulation based on the output signals from the first PPG sensor and the second PPG sensor.

4. The system of claim 3, wherein the one or more hardware processors are configured to:
- determine, based on the output signals from the first PPG sensor and the second PPG sensor, whether an episode of atrial fibrillation is occurring or is likely to occur in the subject; and
- responsive to a determination that atrial fibrillation is occurring or is likely to occur, control the pressure generator to adjust the pressure levels during one or both of inhalation and exhalation to facilitate the pulmonary and systemic circulation, and discourage or prevent the episode of atrial fibrillation.

5. The system of claim 4, wherein the first PPG sensor is a sublingual PPG sensor configured to generate output signals that convey information related to a pulsation of a sublingual vein modulated by a respiration cycle of the subject, and the second PPG sensor is a systemic PPG sensor configured to removably couple with a forehead, temple, ear, or finger of the subject.

6. The system of claim 5, wherein determining, based on the output signals from the first PPG sensor and the second PPG sensor, whether an episode of atrial fibrillation is occurring or is likely to occur in the subject includes determining a transpulmonary delay/transfer time of a blood wave in a pulmonary circulation system of the subject, the delay/transfer time corresponding to an amount of accumulated blood in a right atrium, pulmonary veins, and left atrium of the subject.

7. The system of claim 3, wherein the one or more hardware processors are further configured to cause adjustment, by the pressure generator, of the pressure levels of the pressurized flow of breathable gas during one or both of inhalation and exhalation by amounts that correspond to an amount of venous blood accumulation during cardiac pre-load and/or an amount of cardiac hypervolemic stress in the subject.

8. The system of claim 3, wherein the one or more hardware processors are further configured to:
- responsive to determining that an overload of the right atrium has occurred, cause the pressure generator to increase the pressure level during inhalation above the level indicated by the pressure support therapy regime and cause oscillation of the pressure about the increased pressure level with a timing that corresponds to systolic and diastolic phases of a cardiac cycle in the subject; and
- responsive to determining that an overload of the left atrium has occurred, cause the pressure generator to:
  - adjust the pressure levels during inhalation and exhalation such that the pressure level during exhalation is higher than the pressure level during inhalation; and
  - oscillate the pressure about the adjusted pressure levels during inhalation and exhalation with an oscillation amplitude that is larger during exhalation than inhalation, and with an oscillation timing that corresponds to the systolic and diastolic phases of the cardiac cycle.

9. A method for measuring atrial stretch in a subject with a sensing and monitoring system based on one or more hemodynamic parameters, the system comprising one or more sensors and one or more hardware processors, the method comprising:
- generating, with the one or more external photoplethysmography (PPG) sensors, output signals, during ventilation of the subject, conveying information related to hemodynamic activity in the subject;
- determining, with the one or more hardware processors, the one or more hemodynamic parameters based on the output signals;
- determining, with the one or more hardware processors, a change in the atrial stretch indicative of an overload of a right and/or left atrium in the subject during ventilation based on the on the one or more determined hemodynamic parameters; and
- providing an output for adjusting, based on a determination that an overload of the right and/or left atrium of the subject has occurred, ventilation pressure provided by a ventilation support system.

10. The method of claim 9, wherein the one or more external sensors comprise a first PPG sensor configured to obtain data at a first location on the subject and a second PPG sensor configured to obtain data at a second location on the subject, the second location differing from the first location;
- wherein the one or more hemodynamic parameters comprise atrial extra systoles determined based on output signals from the second PPG sensor; the method further comprising:
- responsive to detection of an atrial extra systole, triggering a pressure generator to provide ventilation support to the subject; and
- validating success of the ventilation support based on output signals from the first PPG sensor that indicate reversion of overloading and/or atrial stretch in the subject.

11. The method of claim 9, wherein the one or more external sensors comprise a first PPG sensor configured to obtain data at a first location on the subject and a second PPG sensor configured to obtain data at a second location on the subject, the second location differing from the first location;
- wherein the sensing and monitoring system further comprises a pressure generator that is part of the ventilation support system, the method further comprising:
- generating, with the pressure generator, a pressurized flow of breathable gas for delivery to an airway of the subject according to a pressure support therapy regime, the pressure support therapy regime indicating pressure levels of the pressurized flow of breathable gas provided by the pressure generator during inhalation and exhalation by the subject;
- generating, with the first PPG sensor, output signals conveying information related to venous blood accumulation during cardiac preload in the subject;
- generating, with the second PPG sensor, output signals conveying information related to heart activity and/or systemic arterial circulation in the subject; and
- controlling, with the one or more hardware processors, the pressure generator to adjust the pressure levels of the pressurized flow of breathable gas during one or both of inhalation and exhalation to facilitate the pulmonary and systemic circulation based on the output signals from the first PPG sensor and the second PPG sensor.

12. The method of claim 11, further comprising:
- determining, with the one or more hardware processors, based on the output signals from the first PPG sensor and the second PPG sensor, whether an episode of atrial fibrillation is occurring or is likely to occur in the subject; and
- responsive to a determination that atrial fibrillation is occurring or is likely to occur, controlling, with the one or more hardware processors, the pressure generator to adjust the pressure levels during one or both of inhalation and exhalation to facilitate the pulmonary and systemic circulation, and discourage or prevent the episode of atrial fibrillation.

13. The method of claim 12, wherein the first PPG sensor is a sublingual PPG sensor configured to generate output signals that convey information related to a pulsation of a sublingual vein modulated by a respiration cycle of the subject, and the second PPG sensor is a systemic PPG sensor configured to removably couple with a forehead, temple, ear, or finger of the subject.

14. The method of claim 13, wherein determining, based on the output signals from the first PPG sensor and the second PPG sensor, whether an episode of atrial fibrillation is occurring or is likely to occur in the subject includes determining a transpulmonary delay/transfer time of a blood wave in a pulmonary circulation system of the subject, the transfer time corresponding to an amount of accumulated blood in a right atrium, pulmonary veins, and left atrium of the subject.

15. The method of claim 11, further comprising causing, with the one or more hardware processors, the pressure generator to adjust the pressure levels of the pressurized flow of breathable gas during one or both of inhalation and exhalation by amounts that correspond to an amount of venous blood accumulation during cardiac preload and/or an amount of cardiac hypervolemic stress in the subject.

16. The method of claim 11, further comprising:
responsive to determining that an overload of the right atrium has occurred, causing, with the one or more hardware processors, the pressure generator to increase the pressure level during inhalation above the level indicated by the pressure support therapy regime and cause oscillation of the pressure about the increased pressure level with a timing that corresponds to systolic and diastolic phases of a cardiac cycle in the subject; and
responsive to determining that an overload of the left atrium has occurred, causing, with the one or more hardware processors, the pressure generator to:
adjust the pressure levels during inhalation and exhalation such that the pressure level during exhalation is higher than the pressure level during inhalation; and
oscillate the pressure about the adjusted pressure levels during inhalation and exhalation with an oscillation amplitude that is larger during exhalation than inhalation, and with an oscillation timing that corresponds to the systolic and diastolic phases of the cardiac cycle.

17. A sensing and monitoring system configured to measure atrial stretch in a subject based on one or more hemodynamic parameters, the system comprising:
external means for generating output signals, during ventilation of the subject, conveying information related to hemodynamic activity in the subject;
means for determining the one or more hemodynamic parameters based on the output signals; and
means for determining a change in the atrial stretch indicative of an overload of a right and/or left atrium in the subject during ventilation based on the on the one or more determined hemodynamic parameters; and
means for providing an output for adjusting, based on a determination that an overload of the right and/or left atrium of the subject has occurred, ventilation pressure provided by a ventilation support system.

18. The system of claim 1, wherein the one or more hardware processors are configured to:
determine the change in the atrial stretch based on a time delay derived from the one or more external PPG sensors, the one or more external PPG sensors comprising a sublingual PPG sensor and a systemic PPG sensor;
use the change in the atrial stretch to increase ventilation pressure; and
determine, during subsequent ventilation, a reduced atrial preload.

19. The method of claim 9, wherein the determining the change in the atrial stretch is based on a time delay derived from the one or more external PPG sensors, the one or more external PPG sensors comprising a sublingual PPG sensor and a systemic PPG sensor;
the method comprising:
using the change in the atrial stretch to increase ventilation pressure; and
determining, during subsequent ventilation, a reduced atrial preload.

20. The system of claim 17, wherein the means for determining the change in the atrial stretch determines the change based on a time delay derived from the external PPG means, the one or more external PPG means comprising a sublingual PPG sensor and a systemic PPG sensor;
the system comprising:
means for using the change in the atrial stretch to increase ventilation pressure; and
means for determining, during subsequent ventilation, a reduced atrial preload.

\* \* \* \* \*